(12) United States Patent
Kuusela et al.

(10) Patent No.: US 10,512,790 B2
(45) Date of Patent: Dec. 24, 2019

(54) SYSTEMS AND METHODS FOR GENERATING RADIATION TREATMENT PLANS

(71) Applicant: Varian Medical Systems International AG., Cham (CH)

(72) Inventors: Esa Kuusela, Espoo (FI); Janne Nord, Espoo (FI); Joakim Pyyry, Helsinki (FI); Perttu Niemela, Espoo (FI)

(73) Assignee: Varian Medical Systems International AG., Cham (CH)

( * ) Notice: Subject to any disclaimer, the term of this patent is extended or adjusted under 35 U.S.C. 154(b) by 528 days.

(21) Appl. No.: 15/403,955

(22) Filed: Jan. 11, 2017

(65) Prior Publication Data

US 2018/0193665 A1    Jul. 12, 2018

(51) Int. Cl.
*A61N 5/00* (2006.01)
*A61N 5/10* (2006.01)

(52) U.S. Cl.
CPC ................................. *A61N 5/1031* (2013.01)

(58) Field of Classification Search
CPC .................................................... A61N 5/1031
See application file for complete search history.

(56) References Cited

U.S. PATENT DOCUMENTS

| | | |
|---|---|---|
| 5,394,452 A | 2/1995 | Swerdloff et al. |
| 5,724,400 A | 3/1998 | Swerdloff et al. |
| 8,644,571 B1 * | 2/2014 | Schulte ................ A61N 5/1039 |
| | | 250/307 |
| 9,901,749 B2 | 2/2018 | Van Heteren et al. |
| 2005/0111621 A1 | 5/2005 | Riker et al. |
| 2009/0154644 A1 | 6/2009 | Nord et al. |
| 2009/0326615 A1 | 12/2009 | Nord et al. |
| 2010/0054410 A1 | 3/2010 | Nord et al. |
| 2010/0177871 A1 | 7/2010 | Nord |
| 2010/0232572 A1 | 9/2010 | Nord et al. |
| 2012/0014507 A1 | 1/2012 | Wu et al. |
| 2013/0197878 A1 | 8/2013 | Fiege et al. |
| 2014/0072109 A1 | 3/2014 | Van Heteren et al. |
| 2014/0350863 A1 | 11/2014 | Hartman et al. |
| 2015/0095043 A1 | 4/2015 | Cordero Marcos et al. |
| 2017/0189715 A1 | 7/2017 | Isola et al. |
| 2017/0296840 A1 | 10/2017 | Bokrantz et al. |
| 2017/0340900 A1 | 11/2017 | Moore et al. |
| 2018/0043182 A1 * | 2/2018 | Wu ........................ G06Q 50/24 |

FOREIGN PATENT DOCUMENTS

| | | |
|---|---|---|
| WO | WO2014187866 | 11/2014 |
| WO | WO2014139040 | 4/2015 |
| WO | WO2016001046 | 1/2016 |
| WO | WO2016081916 | 5/2016 |
| WO | WO2016144914 | 9/2016 |

* cited by examiner

*Primary Examiner* — Dani Fox (57) ABSTRACT

Target values for quality metrics associated with the radiation treatment plan are accessed. Cost function contours are generated; each of the cost function contours includes a respective first set of values of the quality metrics calculated with a respective cost function based on a respective one of the target values. A region that includes a second set of values of the quality metrics is defined; the region is bounded by the cost function contours. A final (optimized) radiation treatment plan is selected from a set of radiation treatment plans that have values of the quality metrics that are within the region.

19 Claims, 7 Drawing Sheets

SYSTEMS AND METHODS FOR GENERATING RADIATION TREATMENT PLANS

RELATED U.S. APPLICATION

This application is related to the U.S. application with Ser. No. 15/391,058, filed Dec. 27, 2016, entitled "Selecting a Dose Prediction Model Based on Clinical Goals," hereby incorporated by reference in its entirety.

BACKGROUND

The use of radiation therapy to treat cancer is well known. Typically, radiation therapy involves directing a beam of high energy proton, photon, or electron radiation ("therapeutic radiation") into a target volume (e.g., a tumor or lesion).

Before a patient is treated with radiation, a treatment plan specific to that patient is developed. The plan defines various aspects of the therapy using simulations and optimizations based on past experiences. For example, for intensity modulated radiation therapy (IMRT), the plan can specify the appropriate beam type (e.g., flattening filter free type) and the appropriate beam energy. Other parts of the plan can specify, for example, the angle of the beam relative to the patient, the beam shape, the placement of boluses and shields, and the like. In general, the purpose of the treatment plan is to deliver sufficient radiation to the target volume while minimizing exposure of surrounding healthy tissue to the radiation. Treatment plans are usually assessed with the aid of dose-volume histograms (DVHs) that, generally speaking, represent three-dimensional (3D) dose distributions in two dimensions.

In IMRT, the planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one best suited to achieving the desired outcome.

For example, the planner defines a set of quality metrics, such as target homogeneity, critical organ sparing, and the like, and respective target values $Q_i$ for the metrics. For planning, the metrics are defined such that a smaller value is preferred over a larger value. The planner also defines a relative priority or weight $w_i$ for each of the quality metrics. The task of developing an optimal plan is then formulated as a quadratic cost function C: $C=\text{sum}(w_i(Q_i-q_i)^2)$, where $q_i$ is the value of the quality metric that can be achieved for a particular treatment plan. The optimal plan is determined by minimizing the cost function C.

Often it is not easy to determine an optimal plan based solely on the cost function. For instance, the optimal solution of the cost function may not necessarily describe the clinically best balance between quality metrics, or the 3D dose distribution might have some undesirable features that are difficult to represent as a quality metric.

One way to assist the planner is a knowledge-based approach that automatically generates objective functions so that the resulting plan incorporates and reflects present practices utilized in creating the knowledge base. This typically captures the best practices utilized at a treatment center, but can also be based on larger knowledge bases of well-defined treatments gathered from multiple treatment centers. A treatment plan developed in this manner can be referred to as a balanced plan.

Another way to assist the planner is to use a multi-criteria optimization (MCO) approach for treatment planning. Pareto surface navigation is an MCO technique that facilitates exploration of the tradeoffs between clinical goals. For a given set of clinical goals, a treatment plan is considered to be Pareto optimal if it satisfies the goals and none of the metrics can be improved without worsening at least one of the other metrics. The set of Pareto optimal plans, which also may be referred to as anchor plans, define a Pareto surface related to the set of clinical goals. Movement along the Pareto surface results in tradeoffs between the clinical goals; some metrics will improve at the cost of worsening one or more other metrics. The planner can navigate along the Pareto surface and choose a final (optimized) radiation treatment plan that seems to be the best according to the criteria applied by the planner, or a treatment plan can be selected automatically based on its proximity to the Pareto surface.

Several schemas have been developed for efficient selection of the sample set of radiation treatment plans that will serve as the anchor plans, to minimize and control the distance to the Pareto surface later during navigation. One known schema is referred to as sandwiching. This schema requires that the Pareto surface be convex. However, this is often not the case. Another known schema is referred to as hyperboxing, which is suitable for non-convex Pareto surfaces. Both sandwiching and hyperboxing utilize only the information related to the sample set in addition to some general features of Pareto surfaces, like its convexity (in sandwiching) or the theoretical maximum/minimum bounds on where the Pareto surface can exist (in hyperboxing).

An improvement to current schemas that reduces the uncertainty of the location of the Pareto surface when determining the final (optimized) radiation treatment plan would be valuable.

SUMMARY

Embodiments according to the present invention pertain to the generation of a radiation treatment plan. Target values for quality metrics associated with the radiation treatment plan are accessed. Cost function contours are generated; each of the cost function contours includes a respective first set of values of the quality metrics calculated with a respective cost function based on a respective one of the target values. A region that includes a second set of values of the quality metrics is defined; the region is bounded by the cost function contours. A final (optimized) radiation treatment plan is selected from a set of radiation treatment plans that have values of the quality metrics that are within the region.

In an embodiment, the target values include a first target value and a second target value for quality metrics associated with a radiation treatment plan are accessed. The cost functions include a first cost function contour and a second cost function contour that are generated with a cost function that is used to evaluate radiation treatment plans. The first cost function contour includes a first set of calculated quality metrics that have a centroid that is the first target value, and the second cost function contour includes a second set of calculated quality metrics that have a centroid that is the second value. A third value is calculated using the first and second values. A region that includes a third set of values of the quality metrics is defined according to the third value and the first and second cost function contours.

This methodology, although described in this summary using an example with two target values, two sets of quality metrics, and two cost function contours, is not so limited; it can be extended to multiple dimensions beyond two or three dimensions.

The final (optimized) radiation treatment plan includes values selected from the third set of values of the quality metrics. That is, the final radiation treatment plan is selected from the sample set of radiation treatment plans that have quality metric values that lie within the defined region.

More specifically, in an embodiment, a Pareto surface that is constrained by the cost function contours is determined. The region is bounded by the intersection of the cost function contours and by the maximum values of the quality metrics at points where the Pareto surface contacts the cost function contours.

In another embodiment, a set of radiation treatment plans are accessed from, for example, a knowledge base. Each of the radiation treatment plans has associated quality metric values. Clusters of the quality metric values are identified. Regions based on the clusters are defined. Each region includes a range of values of the quality metrics in a respective cluster. A Pareto surface based on the clusters and bounding the regions is identified. The final radiation treatment plan is generated using the Pareto surface and based on the set of the quality metrics values in one of the regions.

By defining a region or regions as described above, the uncertainty of the location of the Pareto surface when determining the final radiation treatment plan is reduced, because the portion of the Pareto surface that is navigated to determine the final plan is reduced in size. In other words, it is possible to rule out regions that are unlikely to be on or near the Pareto surface (and therefore unlikely to yield a satisfactory radiation treatment plan). Significantly, embodiments according to the invention are useful in cases in which a conventionally determined Pareto surface is convex or non-convex.

In summary, embodiments according to this disclosure provide different ways to use and balance different cost functions so that a user (e.g., a physician or treatment planner) can arrive at a treatment plan that is the most effective (relative to other plans) and with the least (or most acceptable) side effects (e.g., the lowest dose outside of the region being treated). Without this invention, evaluation and balancing of various cost functions is difficult and a user may end up with multiple treatment plans without a clear and/or objective way to select the best treatment plan. Thus, embodiments according to the invention improve the field of radiation treatment planning specifically and the field of radiation therapy in general. Embodiments according to the invention allow more effective treatment plans to be generated quickly, which can be of critical importance considering the urgency of beginning radiation therapy when a patient is diagnosed with disease such as cancer. Also, embodiments according to the invention help improve the functioning of computer systems because, for example, by narrowing the search for a satisfactory treatment plan, fewer computational resources are needed and consumed to develop the plan, meaning also that computer resources are freed up to perform other tasks.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "using," "inputting," "receiving," "generating," "varying," "navigating," "displaying," or the like, refer to actions and processes (e.g., the flowcharts 400 and 600 of FIGS. 4 and 6, respectively) of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices.

Portions of the detailed description that follows are presented and discussed in terms of a method. Although steps and sequencing thereof are disclosed in figures herein (e.g., FIGS. 4 and 6) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Figure 1:
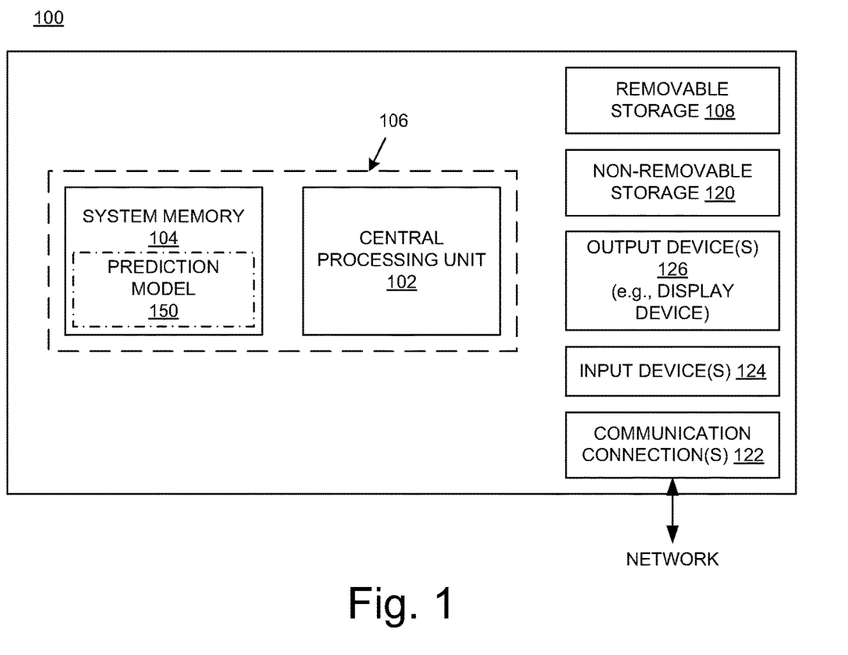
FIG. 1 shows a block diagram of an example of a computing system upon which the embodiments described herein may be implemented.

FIG. 1 shows a block diagram of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with a dose prediction model 150. However, the dose prediction model 150 may instead reside in any one of the computer storage media used by the system 100, or may be distributed over some combination of the computer storage media, or may be distributed over some combination of networked computers.

The dose prediction model 150 may be used to predict dose parameters for a treatment plan corresponding to a particular patient. The dose prediction model 150 may be implemented as a dose-volume histogram (DVH) estimation model, where the predicted quantity is a dose volume histogram. In other embodiments, the prediction model 150 also generates a prediction based on a distance to a target (DTH) histogram, which expresses the distance from a region of interest (ROI) to a radiation target. In yet other embodiments, the dose prediction model 150 is implemented as any other model suitable for predicting dosage (as a dose histogram or spatial 3D dose distribution) for a radiation treatment plan.

The dose prediction model 150 can then be used to develop a radiation treatment plan for a particular patient by receiving patient-specific information (e.g., geometry information) that is input to and processed by the model. The input patient-specific information may contain any combination of parameters that can practically affect the radiation treatment plan. For example, the patient-specific information may be organized as a vector or a data structure including feature elements for: size and shape of the target volume; location of the target volume; size and shape of an organ at risk; type of an organ at risk; a part of the target volume that overlaps an organ; and a part of an organ that overlaps the target volume.

Figure 2:
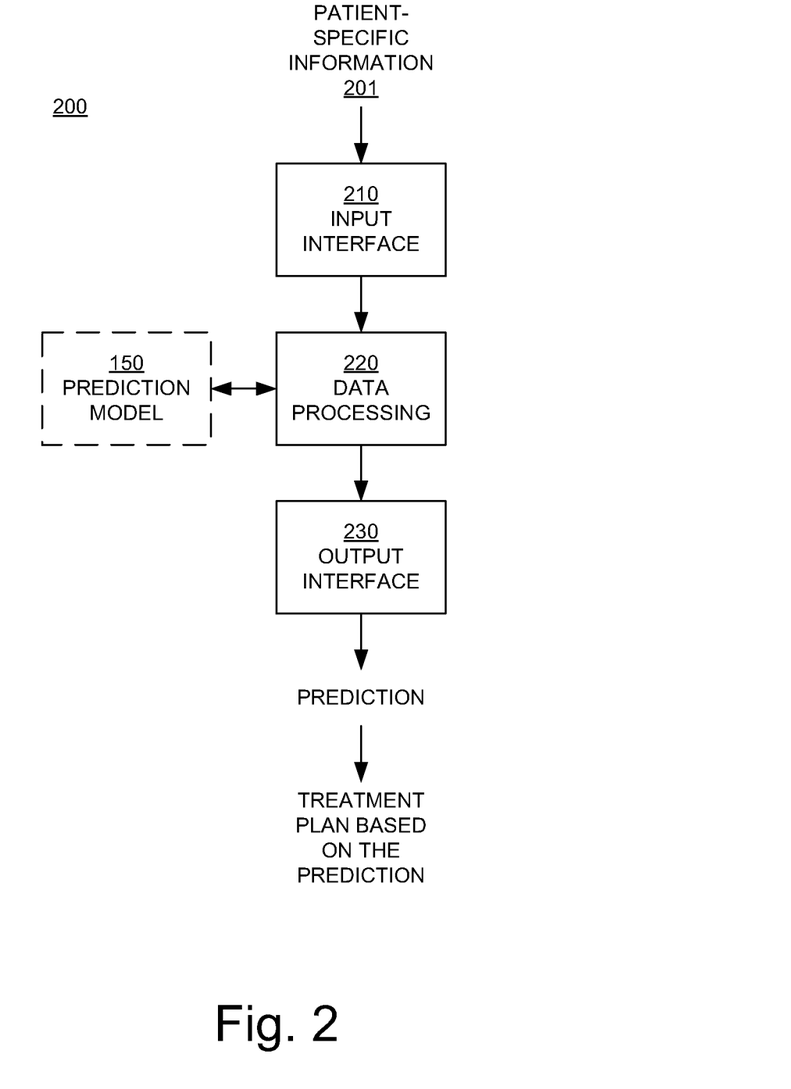
FIG. 2 is a block diagram illustrating an example of an automated radiation treatment planning system in an embodiment according to the present invention.

FIG. 2 is a block diagram illustrating an example of an automated radiation therapy treatment planning system 200 in an embodiment according to the present invention. The system 200 includes an input interface 210 to receive patient-specific information (data) 201, a data processing component 220 that implements the prediction model 150, and an output interface 230. The system 200 in whole or in part may be implemented as a software program, hardware logic, or a combination thereof on/using the computing system 100 (FIG. 1).

The patient-specific information is provided to and processed by the prediction model 150. The prediction model 150 yields a prediction result, e.g., an achievable dose distribution prediction. A treatment plan based on the prediction result can then be generated. In an embodiment, the prediction result is accompanied by parameters indicative of the quality of the prediction, such as reliability of the result (e.g., affected by the internal coherence of the training data), complexity of the predicted plan, and probability of the result.

Figure 3:
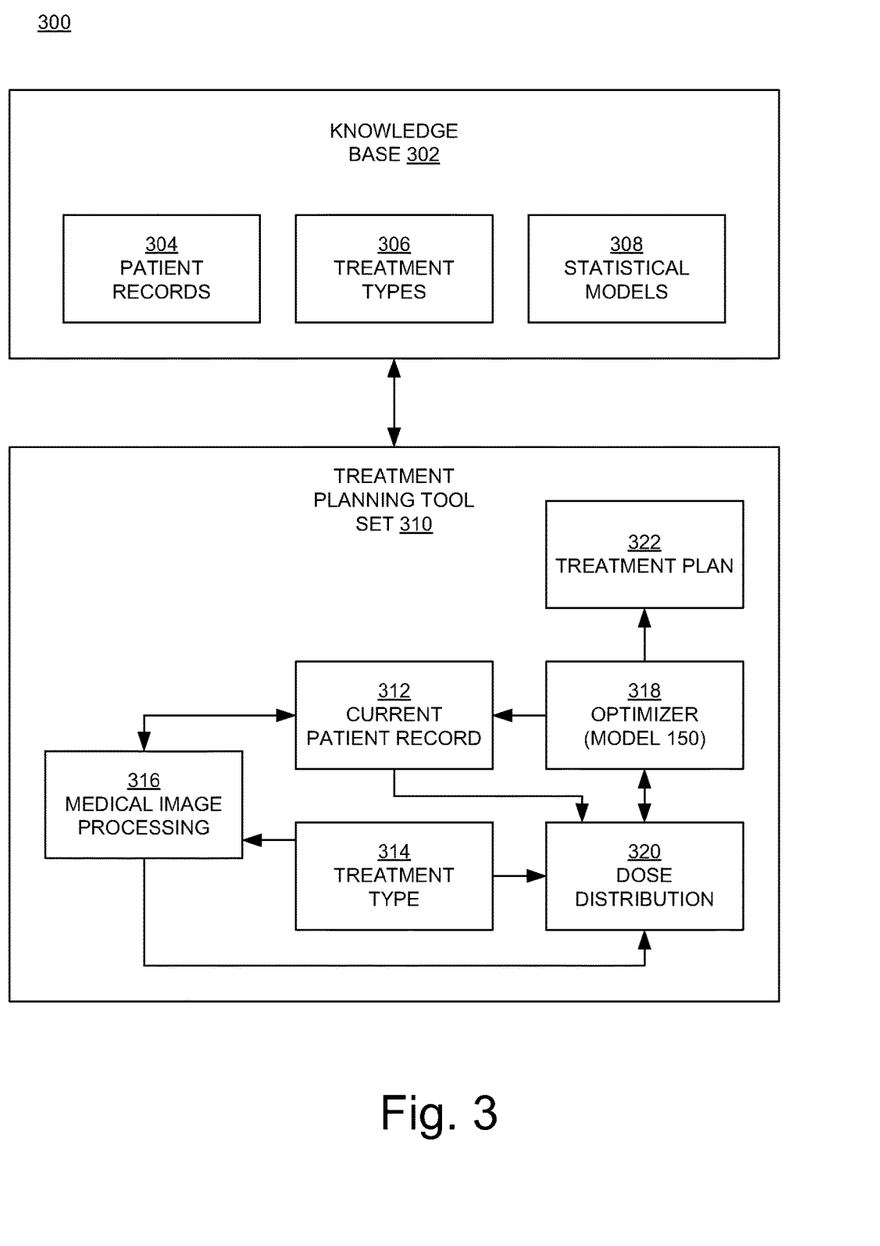
FIG. 3 illustrates an embodiment of a knowledge-based planning system in an embodiment according to the present invention.

FIG. 3 illustrates an embodiment of a knowledge-based planning system 300 incorporating a combination of patient records and statistical models for generating radiation treatment plans in an embodiment according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, an optimizer 318, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322. A radiation treatment plan developed in this manner (e.g., the treatment plan 322) can be referred to as a balanced plan.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. The medical image processing module 316 provides automatic contouring and automatic segmentation of two-dimensional cross-sectional slides (e.g., from computed tomography or magnetic resonance imaging) to form a 3D image using the medical images in the current patient record 312. Dose distribution maps are calculated by the dose distribution module 320.

The knowledge base 302 can be searched for a combination of objectives that can be applied by the optimizer 318 to determine a dose distribution. For example, an average organ-at-risk dose-volume histogram, a mean cohort organ-at-risk dose-volume histogram, and average organ-at-risk objectives can be selected from the knowledge base 302. In embodiments according to the present invention, the optimizer 318 uses the dose prediction model 150 to help shape the dose distribution. Accordingly, the optimizer 318 can provide a 3D dose distribution, fluences, and associated dose-volume histograms for the current patient. By using the dose prediction model 150, which is trained and validated as described above, those results are expected to fall within the historically accepted range for a patient with a similar disease type and treatment type.

Embodiments according to the present invention pertain to the generation of a radiation treatment plan. Target values for quality metrics associated with the radiation treatment plan are accessed. Cost function contours are generated; each of the cost function contours includes a respective first set of values of the quality metrics calculated with a respective cost function based on a respective one of the target values. A region that includes a second set of values of the quality metrics is defined; the region is bounded by the cost function contours. A final (optimized) radiation treatment plan is selected from a set of radiation treatment plans that have values of the quality metrics that are within the region.

Figure 4:
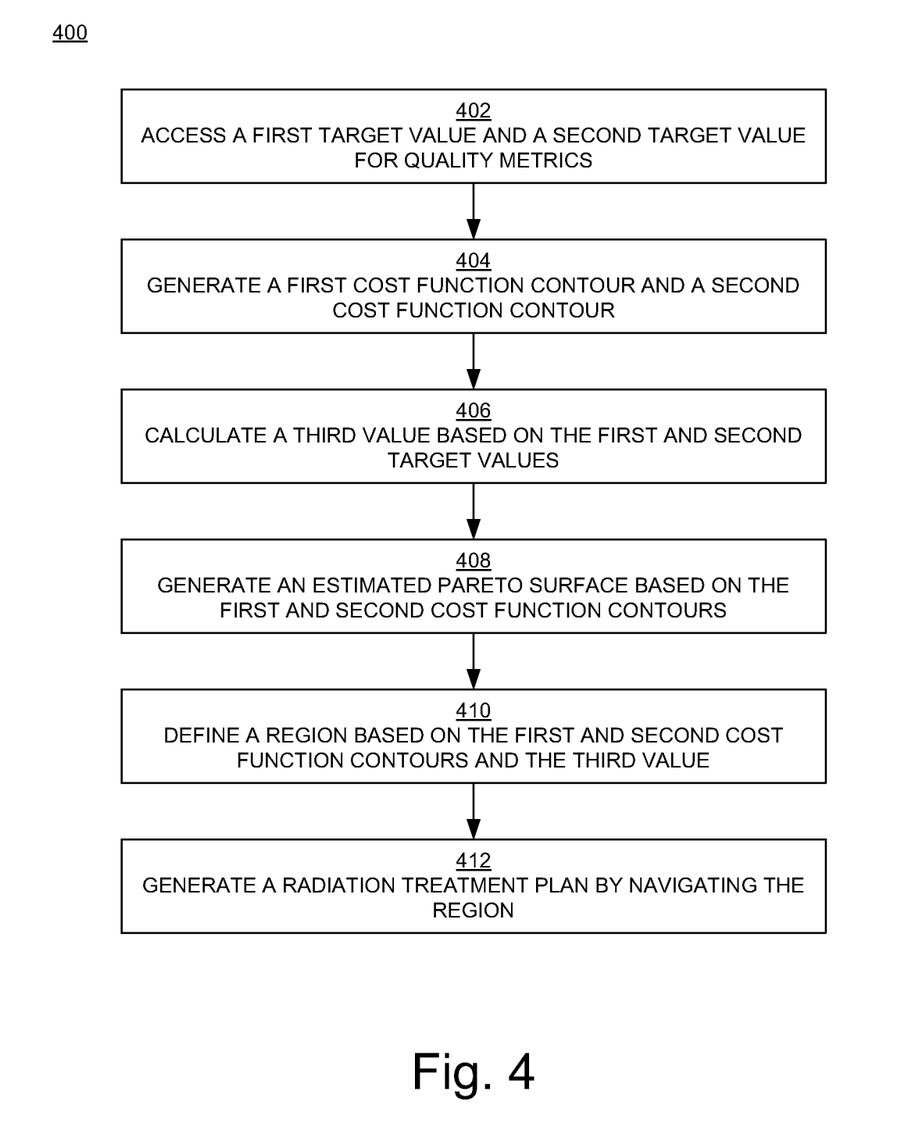
FIG. 4 is a flowchart of an example of a computer-implemented method for generating a radiation treatment plan in an embodiment according to the present invention.

FIG. 4 is a flowchart 400 of an example of a computer-implemented method for generating a radiation treatment plan in an embodiment according to the present invention. The flowchart 400 can be implemented as computer-executable instructions residing on some form of computer-readable storage medium (e.g., using the computing system 100 of FIG. 1).

Figure 5A:
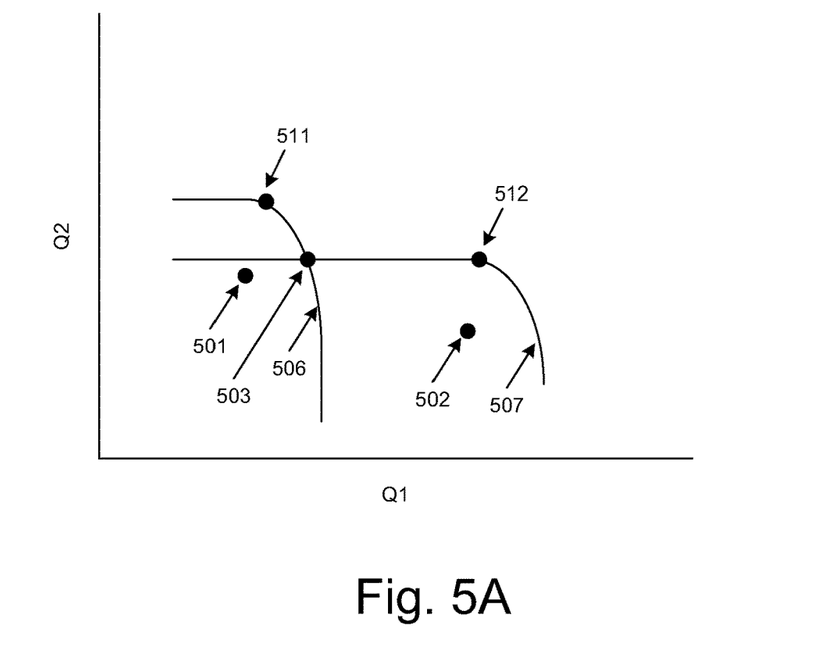
FIGS. 5A and 5B are two-dimensional representations of an example domain of quality metrics in an embodiment according to the present invention.
Figure 5B:
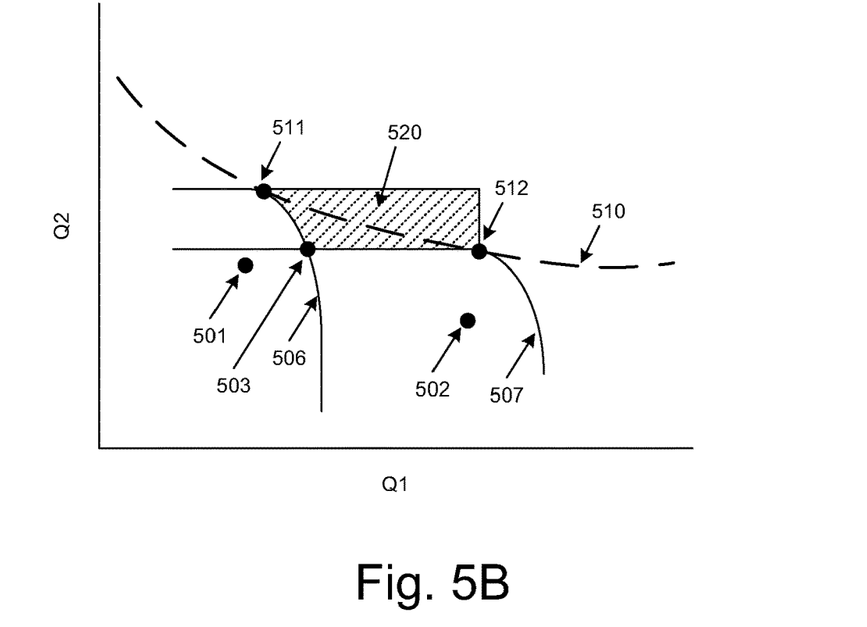

FIG. 4 is discussed in combination with FIGS. 5A and 5B, which illustrate a domain for two quality metrics Q1 and Q2 associated with the radiation treatment plan. In the example of FIGS. 4, 5A, and 5B, only two quality metrics (two dimensions) are described and illustrated; however, the domain may include more than two dimensions (Q1, Q2, . . . , QN). It is not uncommon for seven or more quality metrics to be considered when generating a radiation treatment plan, in which case the domain would have an equal number of dimensions (more than two or three dimensions).

In block 402 of FIG. 4, with reference also to FIG. 5A, a first target value 501 and a second target value 502 for the quality metrics are specified (e.g., by a planner) and accessed. The first target and second target values can be specified by the planner based on, for example, the planner's experience or by accessing the quality metric values for other (e.g., similar) radiation treatment plans in the knowledge base 302 (FIG. 3).

In the example of FIG. 5A, the first target value 501 and the second target value 502 would each include two dimensions: the first target value includes a first value for Q1 and a first value for Q2, and the second target value includes a second value for Q1 and a second value for Q2. Similarly, if the domain included more than two quality metrics, then each target value would include an equal number of values, one for each dimension/quality metric.

In block 404, with reference still to FIGS. 4 and 5A, a first cost function contour 506 and a second cost function contour 507 are generated. In general, an optimal solution for the cost function C is found and then a contour that passes through that solution (point) is determined. In the example of FIG. 5A, the point 511 can be considered the optimal solution for the first cost function $C_1$, and the point 512 can be considered the optimal solution for the first cost function $C_2$. The contours 506 and 507 are defined based on the found optimal solutions (points) 511 and 512. In an embodiment, the first and second cost function contours 506 and 507 are generated with a cost function that is a summation of weighted differences between each one of the target values and each respective one of the calculated quality metrics. In such an embodiment, the first and second cost function contours 506 and 507 are generated with a quadratic cost function: $C_k = \text{sum}(w_{i,k}(Q_{i,k} - q_{i,k})^2)$, where: i=1, 2, . . . , N; k=1 for the first cost function contour and k=2 for the second cost function contour; $w_{i,k}$ is a weight or priority for a respective quality metric Q1, Q2, . . . , QN; $Q_{i,k}$ is the target value for the respective quality metric; and $q_{i,k}$ is the value of the respective quality metric Q1, Q2, . . . , QN that can be achieved for a particular treatment plan. The cost function contours 506 and 507 can be calculated by holding the values of the cost functions $C_k$ constant and then determining combinations of the values of the quality metrics that result in the constant values.

The first cost function contour 506 includes a first set of calculated quality metrics that have a centroid that is the first target value 501, and the second cost function contour 507 includes a second set of calculated quality metrics that have a centroid that is the second value 502.

In the example of FIG. 5A, which includes only two dimensions, the cost function contours are each linear. If, for example, there are three dimensions, then each cost function contour would be planar. If there are more than three dimensions, then each cost function contour can be represented as an appropriately dimensioned hyperplane. Also, the invention is not limited to two centroids (the first and second target values 501 and 502) and two cost function contours; more than two can be used.

In block 406, in an embodiment, a third value 503 is calculated using the first and second values 501 and 502. In general, the third value 503 is at the intersection of the first and second cost function contours 506 and 507. The third value 503 can be calculated as the average of the first and second values 501 and 502. If there are more than two dimensions, then the third value 503 can be determined by minimizing the sum of the distances between the third value and the first and second values 501 and 502.

In block 408, with reference also to FIG. 5B, a Pareto surface 510 is generated. The Pareto surface is an estimated surface that is constrained by the first and second cost function contours 506 and 507. The estimated Pareto surface 510 cannot pass through the first and second cost function contours 506 and 507. As mentioned above, the point 511 where the Pareto surface 510 intersects (touches) the first cost function contour 506 can be considered the optimal solution for the first cost function $C_1$, and the point 512 where the Pareto surface intersects the second cost function contour 507 can be considered the optimal solution for the first cost function $C_2$.

In block 410, with reference also to FIG. 5B, the region 520 is defined. In an embodiment, the region 520 (which is shaded in the figure) is bounded by the first and second cost function contours 506 and 507, by the third value 503, and by the maximum values of the quality metrics Q1 and Q2 at the points 511 and 512 where the Pareto surface 512 contacts the first and second cost function contours. The region 520 includes a third set of values of the quality metrics Q1 and Q2.

In block 412, the final (optimized) radiation treatment plan includes values selected from the third set of values of the quality metrics. That is, the final radiation treatment plan is selected from the sample set of radiation treatment plans that have quality metric values that lie within the defined region 520. The planner can navigate in the region 520 along the Pareto surface 510 and choose a treatment plan that seems to be the best according to the criteria applied by the planner, or a treatment plan can be selected automatically based on its proximity to the Pareto surface.

The information illustrated in FIGS. 5A and 5B can be represented (rendered) in a graphical user interface (GUI) that can be displayed on an output device 126 (a display device) of the computing system 100 (FIG. 1). The GUI can also include a number of interactive sliders that can be used to navigate the Pareto surface 510. Each of the sliders corresponds to a respective quality metric, and the quality metrics can be specified such that a smaller value is better, in which case the sliders are configured so that moving each slider in a given direction (e.g., down) results in an improvement in the corresponding quality metric.

By defining the region 520 as described above, the uncertainty of the location of the Pareto surface 510 when determining the final radiation treatment plan is reduced, because the portion of the Pareto surface that is navigated to determine the final treatment of the plan is reduced in size. In other words, it is possible to rule out regions that are unlikely to be on or near the Pareto surface (and therefore unlikely to yield a satisfactory radiation treatment plan). Instead, the search for a satisfactory radiation treatment plan is narrowed to the solutions contained within the region 520. Also, if it is necessary to generate additional treatment plans, then the parameters (quality metric values) for those plans can be localized to the region 520.

Figure 6:
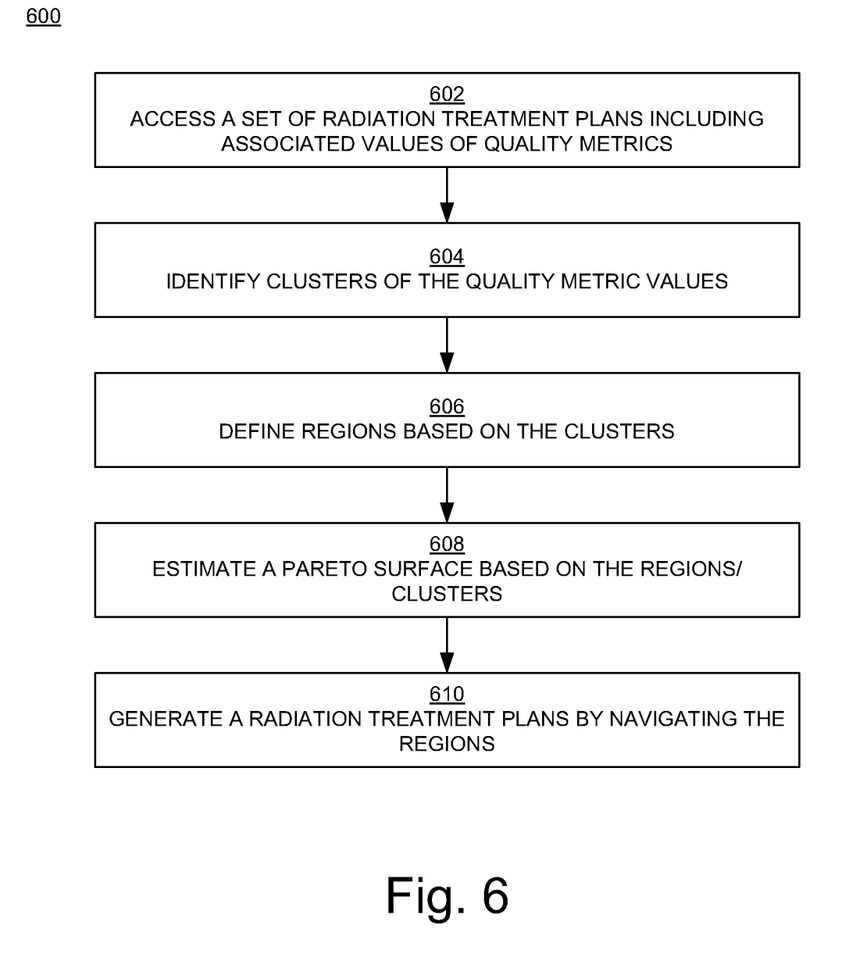
FIG. 6 is a flowchart of an example of a computer-implemented method for generating a radiation treatment plan in another embodiment according to the present invention.

FIG. 6 is a flowchart 600 of an example of a computer-implemented method for generating a radiation treatment plan in another embodiment according to the present invention. The flowchart 600 can be implemented as computer-executable instructions residing on some form of computer-readable storage medium (e.g., using the computing system 100 of FIG. 1).

Figure 7A:
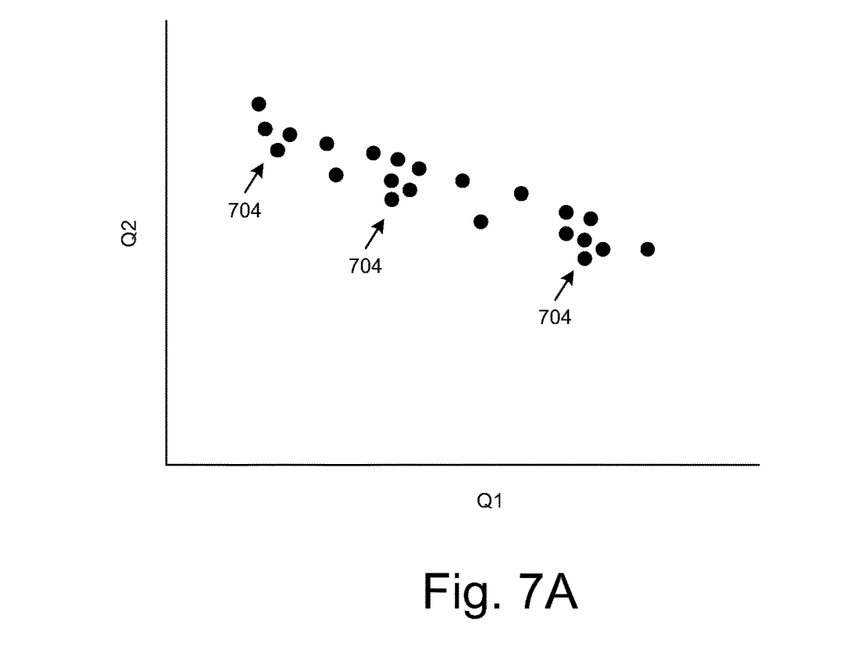
FIGS. 7A and 7B are two-dimensional representations of an example domain of quality metrics in another embodiment according to the present invention.
Figure 7B:
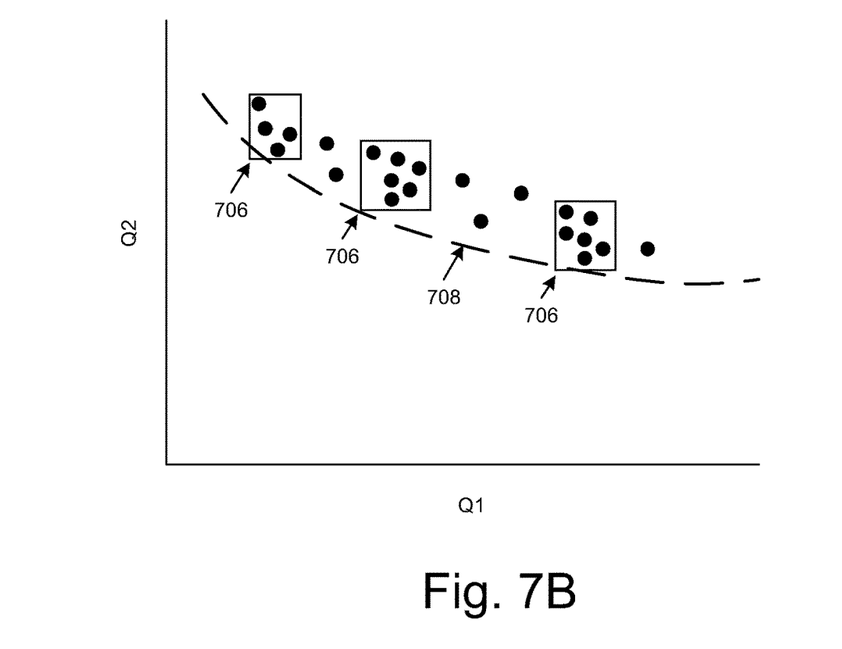

FIG. 6 is discussed in combination with FIGS. 7A and 7B, which illustrate a domain for two quality metrics Q1 and Q2 associated with the radiation treatment plan. As mentioned above, while only two quality metrics (two dimensions) are described and illustrated in the example of FIGS. 6, 7A, and 7B, the domain may include more than two dimensions, and it is not uncommon for seven or more quality metrics to be considered when generating a radiation treatment plan, in which case the domain would have an equal number of dimensions (more than two or three dimensions).

In block 602 of FIG. 6, a set of radiation treatment plans are accessed from, for example, the knowledge base 302 (FIG. 3). Each of the radiation treatment plans includes associated quality metric values.

In block 604 of FIG. 6, with reference also to FIG. 7A, clusters 704 of the quality metric values are identified.

In block 606, with reference also to FIG. 7B, regions 706 based on the clusters 704 are defined. Each region 706 includes a range of values of the quality metrics in a respective cluster.

In block 608, with reference also to FIG. 7B, a Pareto surface 708 based on the clusters 704 and bounding and/or intersecting (e.g., passing through or touching) the regions 706 is identified (estimated).

In block 610, the final radiation treatment plan is generated using the Pareto surface 708. The final radiation treatment plan includes a set of the quality metric values in one of the regions 706. That is, the planner can navigate in one or more of the regions 706 along the Pareto surface 708 and choose a treatment plan that seems to be the best according to the criteria applied by the planner, or a treatment plan can be selected automatically based on its proximity to the Pareto surface.

The information illustrated in FIGS. 7A and 7B can be represented (rendered) in a GUI that can be displayed on an output device 126 (a display device) of the computing system 100 (FIG. 1). The GUI can also include a number of interactive sliders that can be used to navigate the Pareto surface 708, as previously described herein.

Similar to the embodiment of FIGS. 4, 5A, and 5B, by defining the region 706 as just described, the uncertainty of the location of the Pareto surface 708 when determining the final radiation treatment plan is reduced, because the portion of the Pareto surface that is navigated to determine the final treatment of the plan is reduced in size. In other words, it is possible to rule out regions that are unlikely to be on or near the Pareto surface (and therefore unlikely to yield a satisfactory radiation treatment plan). Instead, the search for a satisfactory radiation treatment plan is narrowed to the solutions contained within the regions 706. Also, if it is necessary to generate additional treatment plans, then the parameters (quality metric values) for those plans can be localized to one or more of the regions 706.

In summary, embodiments according to this disclosure provide different ways to use and balance different cost functions so that a user (e.g., a physician or treatment planner) can arrive at a treatment plan that is the most effective (relative to other plans) and with the least (or most acceptable) side effects (e.g., the lowest dose outside of the region being treated). Without this invention, evaluation and balancing of various cost functions is difficult and a user may end up with multiple treatment plans without a clear and/or objective way to select the best treatment plan. Thus, embodiments according to the invention improve the field of radiation treatment planning specifically and the field of radiation therapy in general. Embodiments according to the invention allow more effective treatment plans to be generated quickly, which can be of critical importance considering the urgency of beginning radiation therapy when a patient is diagnosed with disease such as cancer. Also, embodiments according to the invention help improve the functioning of computer systems because, for example, by narrowing the search for a satisfactory treatment plan, fewer computational resources are needed and consumed to develop the plan, meaning also that computer resources are freed up to perform other tasks.

Embodiments according to the invention are thus described. These embodiments can be used to plan different types of external beam radiotherapy other than IMRT including, for example, image-guided radiotherapy (IGRT), RapidArc™ radiotherapy, stereotactic body radiotherapy (SBRT), and stereotactic ablative radiotherapy (SABR).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method for generating a radiation treatment plan, comprising:
    accessing a plurality of values comprising target values for quality metrics associated with the radiation treatment plan;
    generating a plurality of cost function contours, wherein each of the cost function contours comprises a respective first set of values of the quality metrics calculated with a respective cost function based on a respective one of the target values; and
    defining a region comprising a second set of values of the quality metrics, wherein the region is bounded by the plurality of cost function contours, wherein the radiation treatment plan is selected from a set of radiation treatment plans that have values of the quality metrics that are within the region.

2. The method of claim 1, wherein the respective one of the target values is a centroid of a respective cost function contour.

3. The method of claim 1, further comprising determining a Pareto surface that is constrained by the plurality of cost function contours, wherein the cost function contours intersect each other, and wherein the region is bounded by the intersection of the cost function contours and by the maximum values of the quality metrics at points where the Pareto surface contacts the cost function contours.

4. The method of claim 3, wherein the intersection is determined by minimizing distances between the intersection and each of the respective first set of values of the quality metrics.

5. The method of claim 1, wherein each respective cost function comprises a summation of weighted differences between the respective one of the target values and the respective first set of values of the quality metrics.

6. The method of claim 1, further comprising accessing a knowledge base comprising a plurality of radiation treatment plans to determine the target values.

7. The method of claim 1, wherein each of the cost function contours has more than three dimensions.

8. A computing system comprising:
    a central processing unit (CPU); and
    memory coupled to the CPU and having stored therein instructions that, if executed by the computing system, cause the computing system to execute operations to generate a radiation treatment plan, the operations comprising:
        receiving an input comprising a plurality of target values for quality metrics associated with the radiation treatment plan, the target values including a first target value and a second target value;
        generating, with a cost function, a plurality of cost function contours including a first cost function contour and a second cost function contour, wherein the first cost function contour comprises a first set of calculated values of quality metrics based on the first target value, and wherein the second cost function contour comprises a second set of calculated values of the quality metrics based on the second target value; and
        determining a Pareto surface that is constrained by the cost function contours, wherein the cost function contours are used to define a region representing a sample set of radiation treatment plans comprising a third set of values of the quality metrics, and wherein the radiation treatment plan is selected from the sample set.

9. The system of claim 8, wherein the operations comprise calculating a third value using the target values, wherein the third value is an average of the target values.

10. The system of claim 8, wherein the cost function comprises a summation of weighted differences between calculated values of the quality metrics that can be achieved with the radiation treatment plans and the target values.

11. The system of claim 8, wherein the operations further comprise accessing a knowledge base comprising a plurality of radiation treatment plans to determine the target values.

12. The system of claim 8, wherein the cost function contours intersect each other at an intersection, wherein the region is bounded by the intersection and by the maximum values of the quality metrics at points at which the Pareto surface contacts the cost function contours.

13. The system of claim 8, wherein the cost function contours have more than three dimensions each.

14. The system of claim 8, wherein the first set of calculated values of the quality metrics has a centroid that is the first target value and wherein the second set of calculated values of the quality metrics has a centroid that is the second target value, wherein the operations further comprise accessing other target values in addition to the first and second target values that are used as centroids for other cost function contours of the plurality of cost function contours in addition to the first and second cost function contours, and wherein the Pareto surface is also constrained by the other cost function contours.

15. A computing system, comprising:
    a central processing unit (CPU);

memory coupled to the CPU and having stored therein instructions that, when executed by the computing system, cause the computing system to execute a method comprising:

accessing a plurality of radiation treatment plans, each of the radiation treatment plans having a plurality of values of quality metrics associated therewith;

identifying a plurality of clusters of the values of the quality metrics;

defining a plurality of regions based on the clusters, wherein each region of the plurality of regions comprises a range of the values of the quality metrics in a respective cluster of the plurality of clusters;

determining a Pareto surface based on the clusters and bounding the regions; and generating a radiation treatment plan for a patient based on the Pareto surface and comprising a set of the values of the quality metrics in one of the regions.

16. The system of claim 15, wherein the radiation treatment plans are accessed from a knowledge base comprising radiation treatment plans for a plurality of patients.

17. The system of claim 15, wherein the radiation treatment plans are generated using a cost function that is used to evaluate the radiation plans by comparing calculated values of the quality metrics that can be achieved with the radiation plans with target values for the quality metrics.

18. The system of claim 17, wherein the cost function comprises a summation of weighted differences between each one of the target values and each respective one of the calculated quality metrics.

19. The system of claim 15, wherein the regions and the Pareto surface have more than three dimensions each.

* * * * *